United States Patent

Mulhall

Patent Number: 5,258,533
Date of Patent: Nov. 2, 1993

[54] BIS(DIALLYLAMINO) SILANES

[75] Inventor: Steven E. Mulhall, Monroeville Boro, Allegheny County, Pa.

[73] Assignee: Aristech Chemical Corporation, Pittsburgh, Pa.

[21] Appl. No.: 14,880

[22] Filed: Feb. 8, 1993

Related U.S. Application Data

[63] Continuation of Ser. No. 894,970, Jun. 8, 1992, abandoned.

[51] Int. Cl.$^5$ .............................................. C07F 7/10
[52] U.S. Cl. .................................................. 556/410
[58] Field of Search ...................................... 556/410

[56] References Cited

U.S. PATENT DOCUMENTS 3,445,387  5/1969  Liston ........................... 252/32.7

FOREIGN PATENT DOCUMENTS 0423438  4/1991  European Pat. Off. .

OTHER PUBLICATIONS

Giannini et al, Stereospecific Polymerization of Monomers Containing Oxygen and Nitrogen with Ziegler-Natta Catalysts, Polymer Letters, vol. 5, pp. 527-533, (1967).

Giannini et al, Polymerization of Nitrogen-Containing and Oxygen-Containing Monomers by Ziegler-Natta Catalysts, J. Polymer Sci.:Part C 22, pp. 157-175, (1968).

*Primary Examiner*—Paul F. Shaver
*Attorney, Agent, or Firm*—William L. Krayer

[57] ABSTRACT

Bis(diallylamino) silanes of the formula

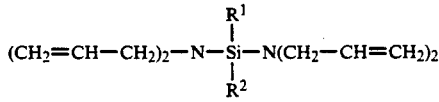

where $R^1$ and $R^2$ are lower alkyl or phenyl groups. The silanes may be homopolymerized or copolymerized with lower olefins and desilylated to exhibit amine functionality.

3 Claims, No Drawings

BIS(DIALLYLAMINO) SILANES

This is a continuation of application Ser. No. 894,970, filed Jun. 8, 1992, now abandoned.

TECHNICAL FIELD

This invention relates to bis(diallylamino) silanes of the general formula

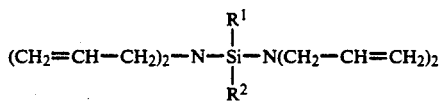

where $R^1$ and $R^2$ are independently selected from alkyl and aryl groups having 1 to 6 carbon atoms. They may be used as cross-linking agents in polymers and find special utility as comonomers for lower olefins polymerized in highly active Ziegler-Natta catalyst systems.

BACKGROUND ART

In European Patent Publication 0423438, Sivak et al propose the use of protected diallyl amine monomers for copolymerization with ethylene, propylene, and other lower alpha-olefins having up to 8 carbon atoms. Protection of the otherwise vulnerable amine group is provided by a silyl group having relatively bulky substituents, such as lower alkyl or phenyl groups. Diallyl amines are proposed and several examples are given of silyl-protected diallyl amines. However, bis-diallyl amines are not contemplated.

SUMMARY OF INVENTION

I have invented new compounds of the general formula

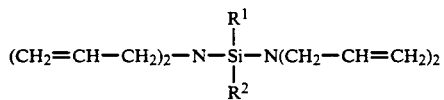

where $R^1$ and $R^2$ are independently selected from alkyl and aryl groups having 1 to 6 carbon atoms. They may be used as cross-linking agents in polymers and find special utility as comonomers for lower olefins polymerized in highly active Ziegler-Natta catalyst systems.

DETAILED DESCRIPTION OF THE INVENTION

My invention will be described with respect to two paradigms, namely bis(diallylamino)dimethylsilane and bis(diallylamino)diphenylsilane.

EXAMPLE I

Bis(diallylamino)dimethylsilane

The equipment used for the synthesis of bis(diallylamino)dimethylsilane was set up in the following manner. A reflux condenser, mechanical stirrer and 125 ml addition funnel were placed on a 2000 ml 3-necked, round-bottomed flask. An argon inlet was connected to the top of the reflux condenser and a heating mantle was placed on the flask. The flask was flushed with argon (allowing the argon to exit the setup through the top of the addition funnel) until the atmosphere in the glassware was assured of being inert.

Heptane (400 ml), triethylamine (136.62 g, 1.350 moles, 188 ml) and diallylamine (98.36 g, 1.012 moles, 125 ml) were charged into the reaction flask. Dichlorodimethylsilane (43.55 g, 0.3375 moles, 41 ml) was placed in the addition funnel and added to the reaction mixture in the flask over a period of 70 minutes. The temperature of the reaction mixture reached 37.5° C. (as measured by a thermocouple between the flask and heating mantle).

The reaction produces a large amount of salts (triethylamine hydrochloride and diallylamine hydrochloride) and twice during the reaction additional heptane had to be added (200 ml portions each time) in order to keep the slurry thinned to a stirrable consistency.

After the addition of dichlorodimethylsilane was complete, the mixture was heated to reflux for five hours. The flask was then allowed to cool to room temperature.

The salts were removed by filtration using a buchner funnel covered with a latex dam to keep exposure to the atmosphere to a minimum. the product was isolated from the filtrate by distillation. The heptane and excess amines were removed at a vacuum of 40 mmHg with a temperature range from ambient to 43° C. The product distilled at 72.6°–74.6° C. at 1 mmHg.

61.2 g of bis(diallylamino)dimethylsilane was isolated by this technique which corresponds to a yield of 72% of theoretical after distillation.

EXAMPLE II

Bis(diallylamino)diphenylsilane

The glassware setup used for the preparation of bis(diallylamino)diphenylsilane was the same as the equipment used for the synthesis of bis(diallylamino)dimethylsilane above except that a 1000 ml flask was used instead of a 2000 ml flask.

After the system was flushed with argon, triethylamine (159.84 g, 1.580 moles, 220.2 ml), diallylamine (84.48 g, 0.8699 moles, 107.3 ml) and toluene (200 ml) were added to the reaction flask. Dichlorodiphenylsilane (100.75 g, 0.3980 moles, 83.7 ml) was charged into the addition funnel and added to the reaction mixture in the flask over a period of 15 minutes, the temperature rose to 60° C.

A large amount of solid precipitated from the mixture. Toluene (100 ml) was added to the flask through the addition funnel to rinse out the remaining silane and make the reaction mixture more stirrable and the mixture was heated to reflux for two hours, then cooled to room temperature.

The salts were removed by filtration using a sealed pressure filter under an inert atmosphere. The product was isolated from the filtrate by distillation. The heptane and excess amines were removed at a vacuum of 40 mmHg with a temperature range from ambient to 43° C. The product distilled in a range from 160°/0.3 mmHg to 160°/0.1 mmHg.

101.5 g of bis(diallylamino)diphenylsilane was isolated by this technique which corresponds to a yield of 68% of theoretical after distillation.

Similar preparations may be made for the diethyl, dipropyl, dibutyl, dipentyl and dihexyl variants.

My new monomers may be incorporated into chains of crystalline polypropylene and other lower olefin polymers as described in the above-mentioned Sivak et al patent. Thereafter, the silyl groups may be removed by hydrolysis or alcoholysis optionally promoted by acidic or basic catalysis and the remaining copolymers, which may be mildly cross-linked, will exhibit amine functionality or ammonium functionality in the presence of acids.

My monomers may be homopolymerized using Ziegler-Natta systems and/or copolymerized in amounts to yield copolymers having ratios of lower olefin to my monomer (m) of 0.1 mole % to 99.9 mole %.

I claim:

1. Bis(diallylamino) silanes of the formula

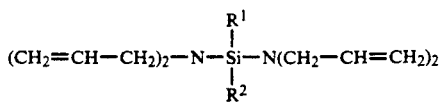

where $R^1$ and $R^2$ are independently selected from alkyl and aryl groups having 1 to 6 carbon atoms.

2. A silane of claim 1 wherein $R^1$ and $R^2$ are $CH_3$.

3. A silane of claim 1 wherein $R^1$ and $R^2$ are phenyl groups.

* * * * *